United States Patent [19]
Yao

[11] Patent Number: 5,989,260
[45] Date of Patent: Nov. 23, 1999

[54] INTRAMEDULLARY NAIL GUIDE ROD WITH MEASURE SCALE MARKED THEREON

[76] Inventor: Meei-Huei Yao, 62, Yung-Luh Rd., Ho-Wei Township, Chang-Hua County, Taiwan

[21] Appl. No.: 08/624,936

[22] Filed: Mar. 27, 1996

Related U.S. Application Data

[63] Continuation of application No. 08/293,591, Aug. 22, 1994, abandoned.

[51] Int. Cl.$^6$ .................................................. A61B 17/17
[52] U.S. Cl. ............................................ 606/102; 606/96
[58] Field of Search .................... 606/62, 63, 64, 606/96, 97, 98, 86, 102

[56] References Cited

U.S. PATENT DOCUMENTS

| | | | |
|---|---|---|---|
| 2,267,925 | 12/1941 | Johnston | 606/104 |
| 4,450,834 | 5/1984 | Fischer | 606/102 |
| 4,474,177 | 10/1984 | Whiteside | 606/62 |
| 4,710,075 | 12/1987 | Davison | 33/512 |
| 4,976,714 | 12/1990 | Aghion | 606/62 |
| 5,013,318 | 5/1991 | Spranza, III | 606/102 |
| 5,109,869 | 5/1992 | Buckley | 33/512 |
| 5,122,146 | 6/1992 | Chapman et al. | 606/102 |
| 5,171,248 | 12/1992 | Ellis | 606/102 |
| 5,234,434 | 8/1993 | Goble et al. | 606/96 |
| 5,681,318 | 10/1997 | Pennig et al. | 606/98 |
| 5,688,284 | 11/1997 | Chervitz et al. | 606/96 |

*Primary Examiner*—Michael Buiz
*Assistant Examiner*—Vy Quang Bui
*Attorney, Agent, or Firm*—Larson & Taylor

[57] ABSTRACT

An intramedullary nail guide rod for surgical treatment of a fractured tibia or femur comprises a hand grip, a sleeve and a graduated guide rod. The sleeve is fastened at one end thereof to the hand grip and provided at another end thereof with a threaded hole. The graduated guide rod has a measuring scale ranging between 0 cm and 70 cm at an interval of 0.5 cm. (length and interval can be increase or reduce according to the operational requirement) The graduated guide rod is provided at one end thereof with a fastening slot engageable with the threaded hole of the sleeve in conjunction with a fastening bolt. The graduated guide rod is further provided at another end thereof with a disk head.

3 Claims, 7 Drawing Sheets

INTRAMEDULLARY NAIL GUIDE ROD WITH MEASURE SCALE MARKED THEREON

This application is a continuation of application Ser. No. 08/293,591 filed Aug. 22, 1994, now abandoned.

BACKGROUND OF THE INVENTION

The present invention relates generally to a bone fixing device and more particularly to an intramedullary nail (abbreviated as IMN) guide rod with a measuring scale marked thereon.

According to the conventional surgical operation for treating a fractured tibia or femur, an intramedullary nail is implanted in the marrow of the tibia or femur under treatment. Thereafter, the operating surgeon must be assisted by a C-arm X-ray machine for locating the position of the screw hole for a locking screw. The operating surgeon makes use of two identical round rods, one of which is implanted into the intramedullary nail. The drilling accuracy of the screw hole is then determined with the naked eye by the depth at which a K-pin is touched by the implanted round rod. The locking screw is then fastened onto the fractured tibia or femur.

Such a conventional method as described above is defective in design in that the operating surgeon is hazardously exposed to the X ray emitted by the C-arm X-ray machine during the operation, and that the inspection of the screw hole position done by the naked eye with two round rods is prone to a human error, thereby causing the intramedullary nail to penetrate the joint. In addition, it is likely that the implanted guide rod can not be taken out easily from the intramedullary nail whose outer diameter is improperly small.

SUMMARY OF THE INVENTION

It is therefore the primary objective of the present invention to provide an imtramedullary nail guide rod, which has a measuring scale marked thereon to facilitate the surgical operation for treating a fractured tibia or femur.

In keeping with the principle of the present invention, the foregoing objective of the present invention is attained by an intramedullary nail guide rod, which comprises a hand grip to which a sleeve is fastened. The sleeve is provided with a threaded hole for fastening a guide rod having a length measuring scale marked thereon and having at the front end thereof a disk head.

The objective, features and functions of the present invention will be more readily understood upon a thoughtful deliberation of the following detailed description of the present invention in conjunction with the accompanying drawings.

DETAILED DESCRIPTION OF THE INVENTION

Figure 1:
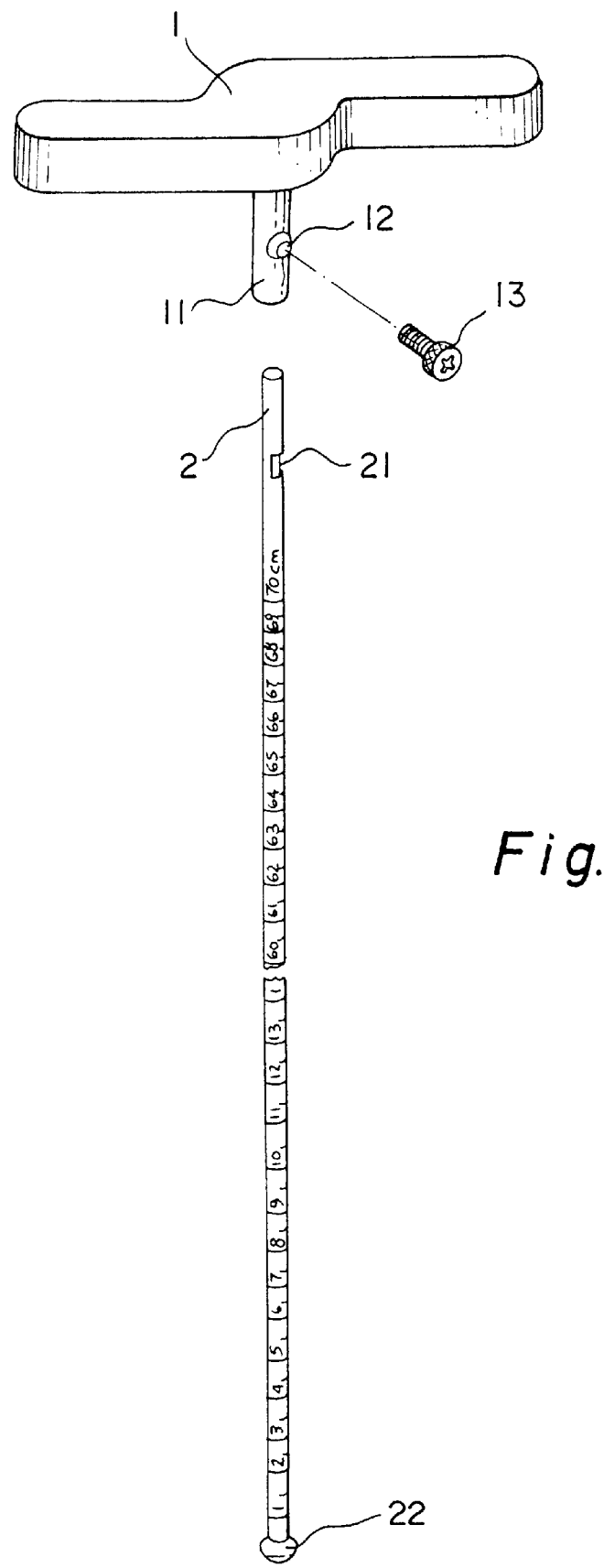
FIG. 1 shows an exploded view of the present invention.
Figure 2:
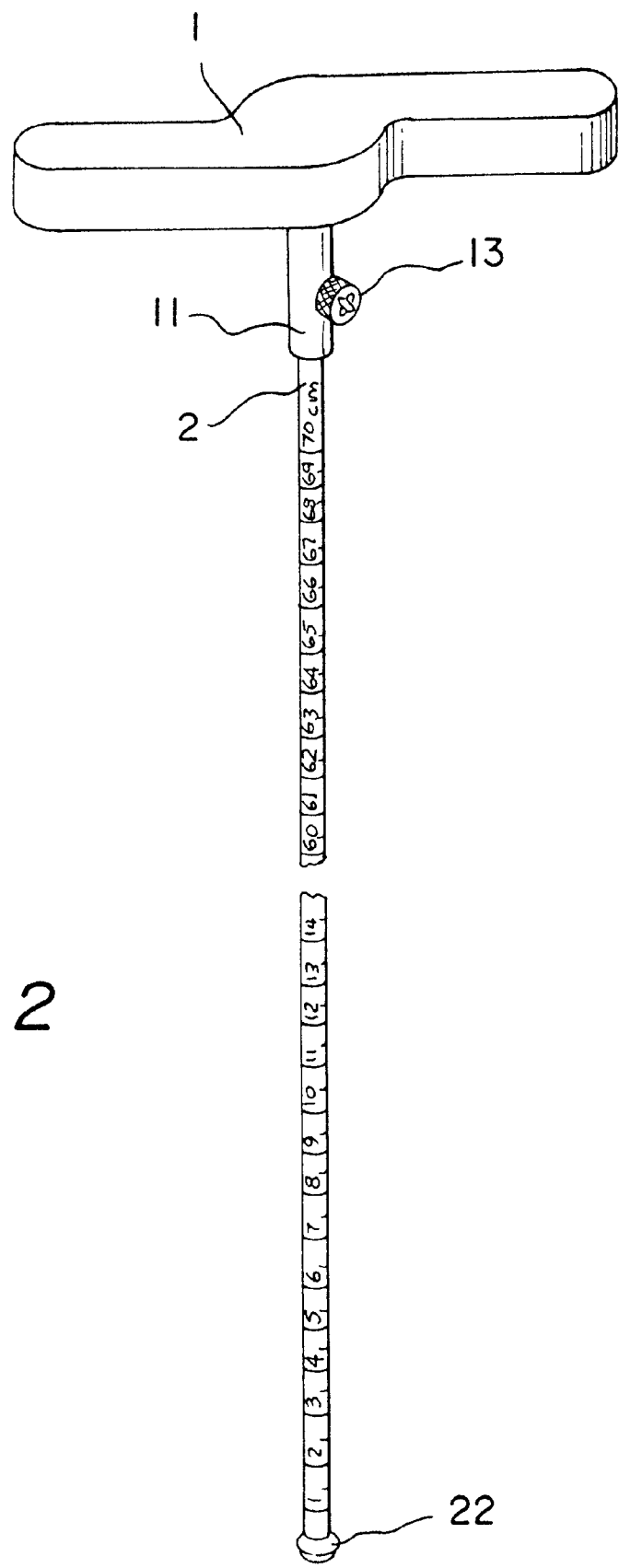
FIG. 2 shows a perspective view of the present invention in combination.

As shown in FIGS. 1 and 2, there is provided a hand grip 1 with a sleeve 11 fastened centrally thereto. The sleeve 11 is provided at an appropriate position thereof with a threaded hole 12 for fastening a guide rod 2 in conjunction with a bolt 13. The guide rod 2 of a predetermined length is provided thereon with a series of marks ranging from 0 cm to 70 cm at an interval of 0.5 cm. (length and interval can be increased or reduced according to the operational requirement) The guide rod 2 is provided at the rear end thereof with a fastening slot 21 and at the front end thereof with a disk head 22. In combination, the rear end of the guide rod 2 is inserted into the open end of the sleeve 11 such that the fastening slot 21 of the guide rod 2 is fastened with the threaded hole 12 by means of the bolt 13, as shown in FIG. 2.

Figure 3A:
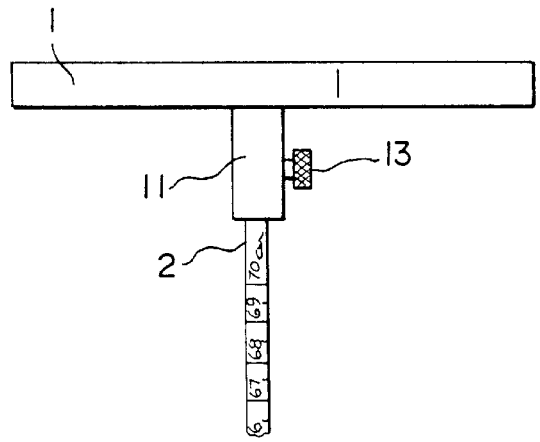
FIG. 3A shows an exploded view of the scale marks on the guide rod for determining length of the bone screw.
Figure 3A:
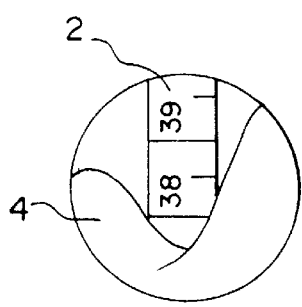
Figure 3:
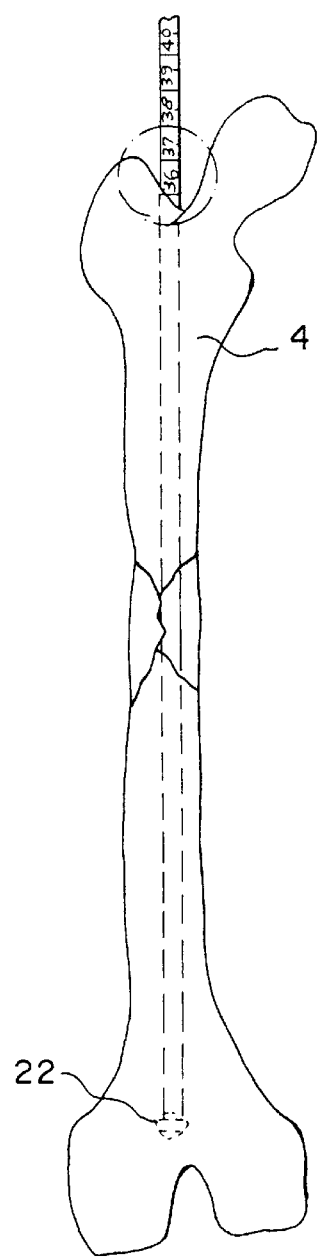
FIG. 3 shows a schematic view of the retrieving action of the present invention.
Figure 4A:
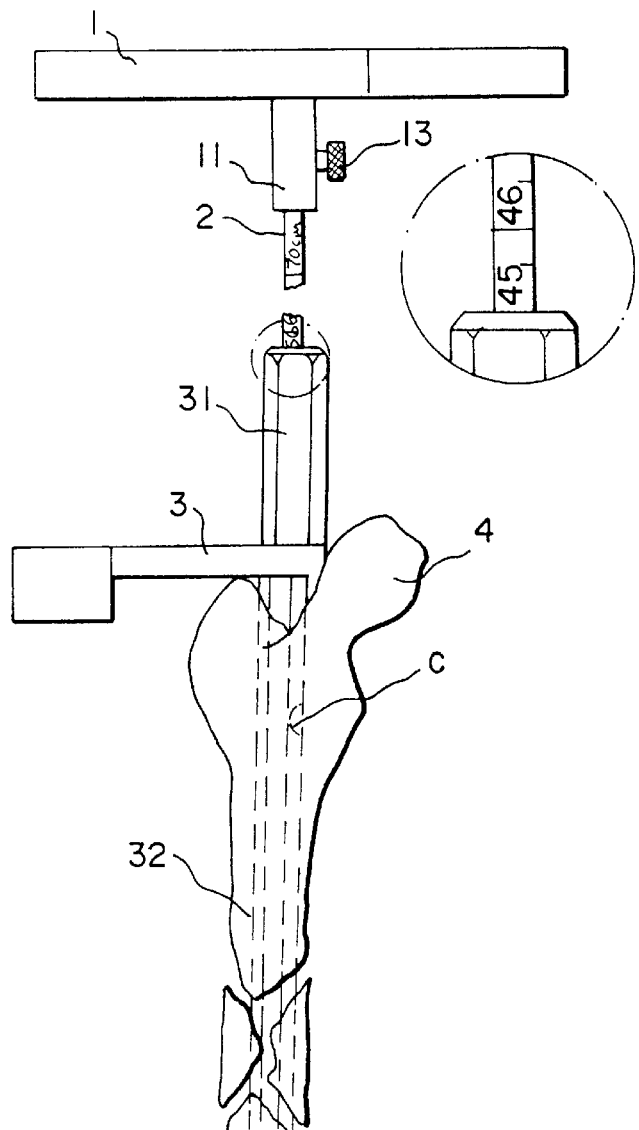
FIG. 4A shows an exploded view of the scale marks on the guide rod during a determination of location of a first drilling hole. invention.
Figure 4:
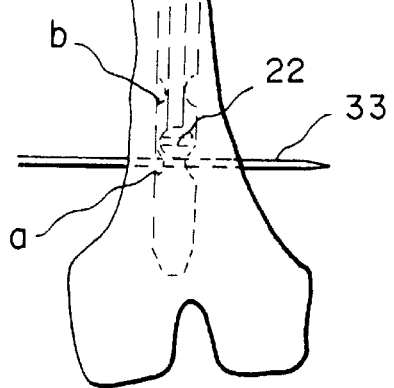
FIG. 4 shows a schematic view of another action of the present
Figures 5, 5A:
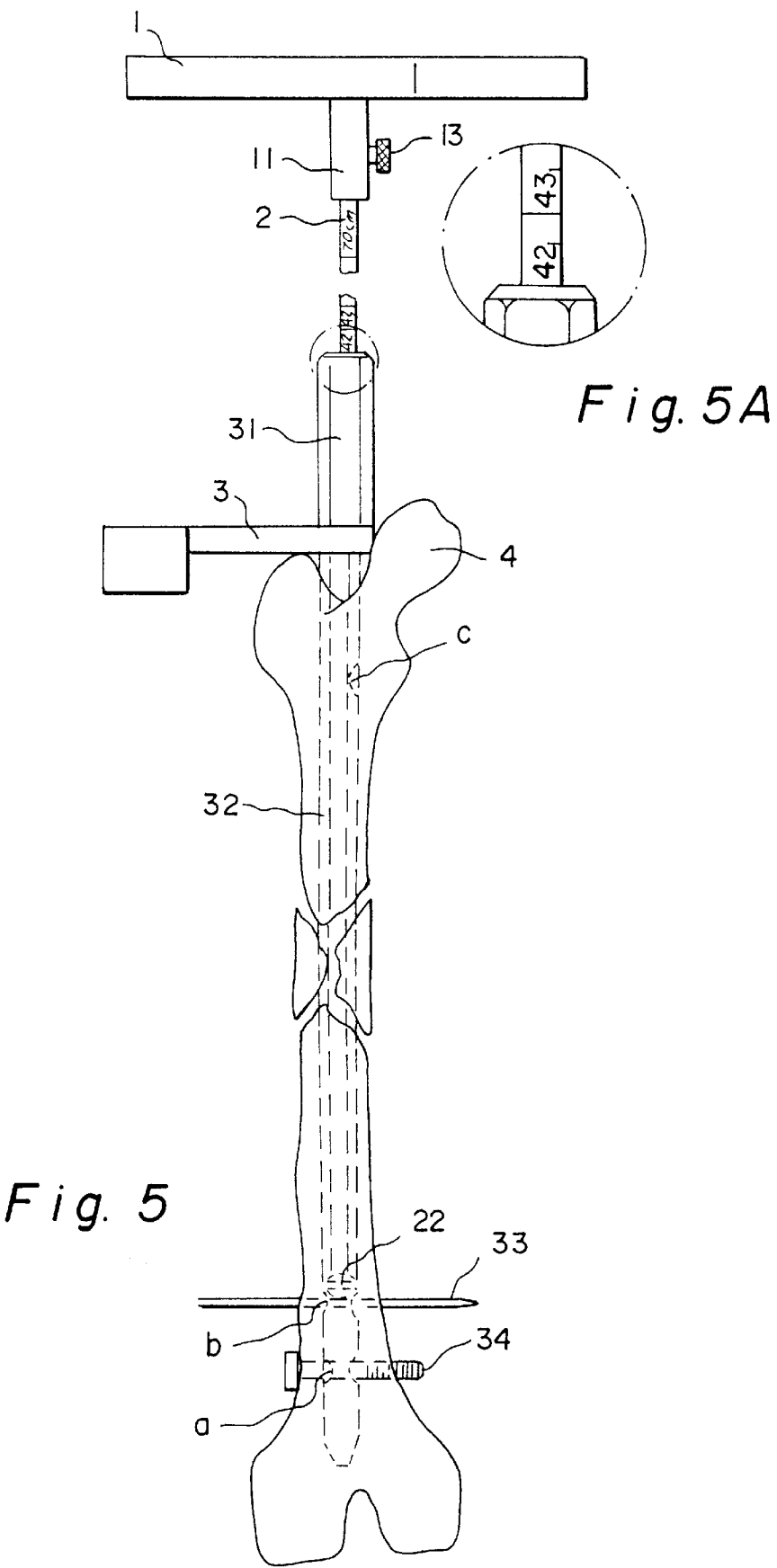
FIG. 5 shows a schematic view of the action of the present invention.
FIG. 5A shows an exploded view of the scale marks on the guide rod during a determination of location of a second drilling hole.
Figures 6, 6A:
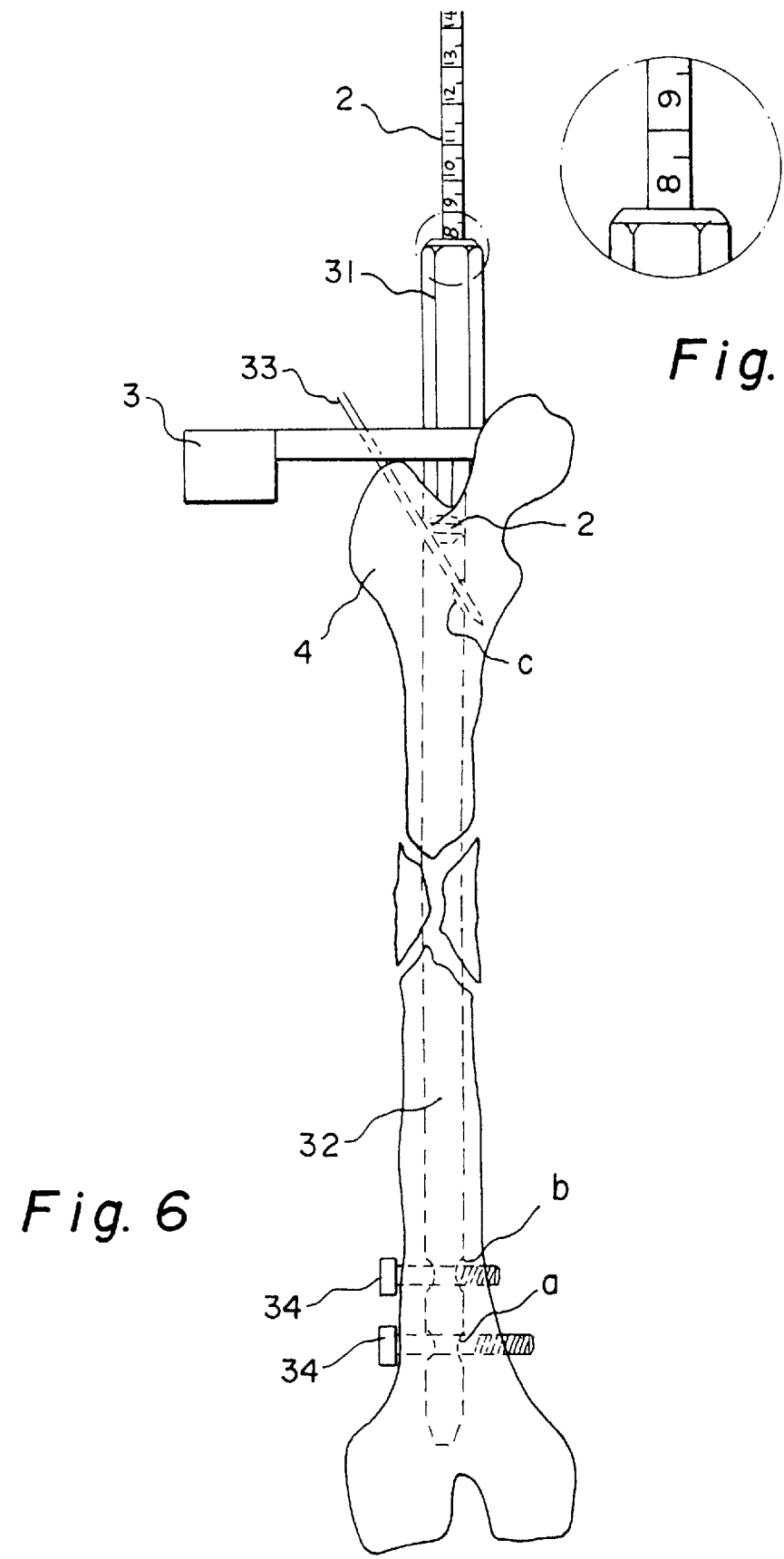
FIG. 6 shows a schematic view of the action of the present invention.
FIG. 6A shows an exploded view of the scale marks on the guide rod during a determination of location of a third drilling hole.
Figure 7:
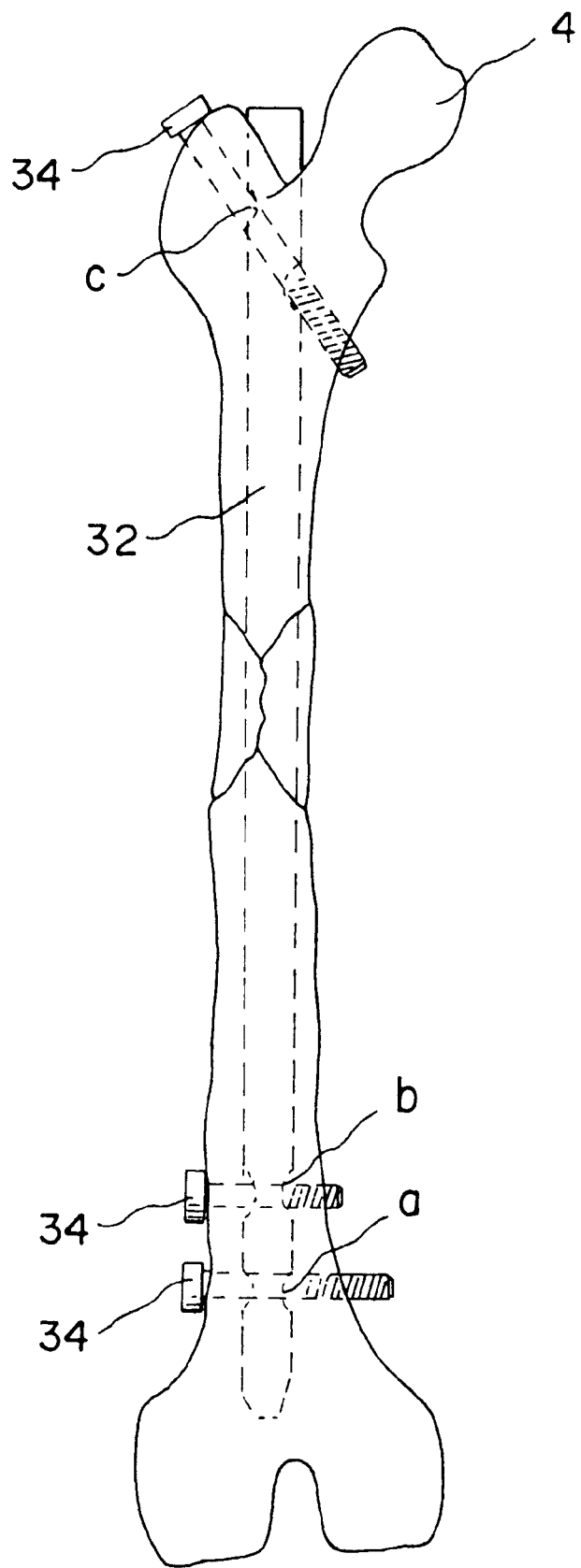
FIG. 7 shows a schematic view of the conclusion of the action of the present invention.

As shown in FIGS. 3, and 3a the length of the bone screw can be determined by the scale marks of the portion of the guide rod 2 over the top end of the retrieved tibia or femur. As shown in FIGS. 4 and 5, an intramedullary nail 32 is first fixed by the locking rod 31 of a fixation frame 3 before the intramedullary nail 32 is implanted into the bone marrow. A 1.8 m/m or 2.0 m/m K-pin 33 is put through horizontally the fractured tibia or femur. The guide rod 2 is moved slowly into the longitudinal hole of the intramedullary nail 32. The orientation and the movement of the guide rod 2 can be adjusted with precision by the hand grip 1 such that the disk head 22 of the guide rod 2 is stopped by the K-pin 33.The accuracy of the position of the drilling hole can be determined by the scale marks of the portion of the guide rod 2 over the locking rod 31, as shown in FIG. 4A. Thereafter, the drilling is done according to the sizes of a, b, and c holes. The locking screws 34 are then fastened into the holes, as shown in FIGS. 5, 6, and 7. The operation of the bone fixation is then completed with ease and speed.

The present invention has several inherent advantages, which are expounded explicitly hereinafter.

The present invention has retrieving and guiding functions.

The present invention permits the selection of an intramedullary nail having a safe length. The appropriate length of the intramedullary nail can be determined by the scale marks of the portion of the guide rod over the top end of the fractured tibia or femur without having to use another guide rod to compare the length.

The present invention has a reaming function and is suitable for use in all types of reamers that are currently in use. The disk head of the present invention can prevent the injury of the joint.

The present invention is helpful in aiming precisely the locking screw at the hole of the intramedullary nail by observing the change in the scale marks of the guide rod without having to rely on the X-ray machine or another guide rod for making a length comparison.

The present invention is suitable for use in all intramedullary nails having various diameters. The guide rod of the present invention can be easily removed from the intramedullary nail.

The present invention makes use of only one guide rod having a scale marked thereon. As a result, there is no need to use another guide rod for making a length comparison.

The guide rod of the present invention is provided thereon with a measuring scale and can therefore speed up the surgical operation. In addition, the present invention improves the accuracy and the safety of the surgical operation.

The present invention is suitable for use in the fixation operation of the intramedullary nails made by various corporations.

The orientation and the up-and-down movement of the guide rod of the present invention can be precisely adjusted by the hand grip to which the guide rod is fastened.

The embodiment of the present invention described above is to be regarded in all respects as merely illustrative and not restrictive. Accordingly, the present invention may be embodied in other specific forms without deviating from the spirit hereof. The present invention is therefore to be limited only by the scope of the following appended claim.

What is claimed is:

1. An intramedullary nail guide rod for surgical treatment of a fractured tibia or femur comprising:

a graduated rod having dimensions suitable for insertion into an intramedullary nail in a fractured tibia or femur, a length of said guide rod exceeding that of said intramedullary nail, said guide rod having a disk head at a first end thereof, said disk head having a diameter exceeding a diameter of said graduated guide rod for preventing movement of said guide rod beyond a depth at which a K-pin is inserted in a fractured tibia or femur, said graduated guide rod including a measuring scale along a longitudinal length thereof, said measuring scale extending outside of said intramedullary nail when said guide rod is inserted into said intramedullary nail; and a hand grip attached to a second end of said guide rod opposite said first end for adjusting movement and orientation of the guide rod in said intramedullary nail, said hand grip including a sleeve for receiving the second end of said guide rod, said sleeve including a threaded aperture alignable with a fastening slot in said second end of said guide rod for receiving fastening means for fastening said guide rod to said hand grip.

2. A method of securing an intramedullary nail in a fractured tibia or femur comprising the steps of:

inserting a guide rod into an intramedullary nail while adjusting and orienting said guide rod by means of a hand grip attached to an end of said guide rod, movement of said guide rod into said intramedullary nail being limited by a disk head at an opposite end of said guide rod, said disk head having a diameter exceeding a diameter of said guide rod;

determining a position of a drilling hole by means of scale marks along a longitudinal length of said guide rod;

drilling a screw hole in said fractured bone; and inserting a screw in said screw hole.

3. A method of securing an intramedullary nail in a fractured tibia or femur using an intramedullary nail guide rod comprising a graduated guide rod having a disk head at a first end thereof, said disk head having a diameter exceeding a diameter of said guide rod, a hand grip attached to a second, opposite end of said guide rod and a measuring scale along a longitudinal length of said guide rod, said method comprising the steps of:

inserting the guide rod into an intramedullary nail of a fractured bone up to a point at which said disk head is stopped by a K-pin while adjusting and orienting said guide rod by means of said hand grip;

determining a position of a drilling hole by means of the measuring scale on said guide rod;

drilling a screw hole in the fractured bone; and inserting a screw in said screw hole.

* * * * *